United States Patent [19]

Adrian et al.

[11] 4,067,905
[45] Jan. 10, 1978

[54] PREPARATION OF 2-AMINO-N-BUTANOL

[75] Inventors: Guy Adrian, Lille; Marcel-Xavier Sion, Douai; André Benattar, Lille, all of France

[73] Assignee: Societe Chimique de la Grande Paroisse, Azote et Produits Chimiques, Paris, France

[21] Appl. No.: 650,695

[22] Filed: Jan. 20, 1976

[30] Foreign Application Priority Data

Feb. 4, 1975 France .................................. 75.03431
Nov. 13, 1975 France .................................. 75.34567

[51] Int. Cl.$^2$ .............................................. C07C 91/04
[52] U.S. Cl. .................................................. 260/584 R
[58] Field of Search ...................... 260/584 R, 583 M

[56] References Cited

U.S. PATENT DOCUMENTS

| | | | |
|---|---|---|---|
| 3,534,112 | 10/1970 | Tindall | 260/584 R X |
| 3,546,298 | 12/1970 | Tindall | 260/584 R |
| 3,564,062 | 2/1971 | Tindall | 260/584 R X |
| 3,736,265 | 5/1973 | Suggitt | 260/583 M X |
| 3,739,027 | 6/1973 | Gates | 260/583 M |
| 3,801,640 | 4/1974 | Knifton | 260/583 M X |

OTHER PUBLICATIONS

Fieser and Fieser, "Reagents for Organic Synthesis", copyright 1967, pp. 1252–1254.
Hirst et al., "J. Chem. Soc.", pp. 924–920 (1947).

*Primary Examiner*—Daniel E. Wyman
*Assistant Examiner*—John J. Doll
*Attorney, Agent, or Firm*—Browdy and Neimark

[57] ABSTRACT

2-Amino-n-butanol is prepared by condensing 1-nitropropane with formaldehyde in an aqueous medium in the presence of a phase transfer agent which acts both as a basic catalyst and as a surfactant, and the resulting 2-nitro-n-butanol obtained is subjected to catalytic hydrogenation using a hydrogenating mixture consisting of hydrogen and nitrogen at a pressure of 8 to 12 bars.

11 Claims, No Drawings

PREPARATION OF 2-AMINO-N-BUTANOL

This invention relates to the production of 2-amino-n-butanol.

BACKGROUND OF THE INVENTION

It is known to produce 2-amino-n-butanol by condensing 1-nitropropane with formaldehyde and then to reduce the nitro group in the resulting 2-nitro-n-butanol by reductive hydrogenation. However, the yields in these two reactions are not particularly satisfactory, especially that obtained in the condensation of 1-nitropropane with formaldehyde to 2-nitro-n-butanol.

1-Nitropropane (I) reacts with formaldehyde in the presence of a basic catalyst to form a mixture of 2-nitro-n-butanol (III) and 2-nitro-2-ethylpropane-1,3-diol (III).

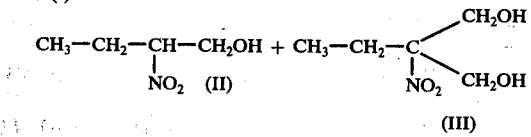

Therefore, attempts have been made to increase the proportion of 1-nitropropane converted and to improve the yield of 2-nitro-1-butanol obtained in the condensation, as well as the yield from the hydrogenation, particularly when the formylation in the presence of a base takes place in an aqueous medium.

DETAILED DESCRIPTION OF THE INVENTION

Reaction conditions have now been determined which enable 2-amino-n-butanol to be obtained in satisfactory yields for industrial production, the proportion of 1-nitropropane converted being at least 60%.

In accordance with the invention, the 1-nitropropane is formylated in an aqueous medium in the absence of solvents but in the presence of a phase transfer agent which also acts as a catalyst for the formylation and a surfactant. The phase transfer agent is present in minor proportion relative to the reactants.

The phase-transfer agent which catalyses the formylation is selected from the group consisting of quaternary ammonium hydroxides and tertiary amines.

The quaternary ammonium hydroxide may be of the general formula $(R)_4 N^+ OH^-$ in which each R is an alkyl group containing 2 to 12 carbon atoms. However the general formula is preferably $R_1 R_2 R_3 R_4 N^+ OH^-$, in which $R_1$, $R_2$, $R_3$ and $R_4$ are like or unlike groups, the four groups being, for example, all ethyl or all butyl groups, or $R_1$ being an aryl substituted alkyl group such as a benzyl group or, alternatively, an octyl or dodecyl group whilst the other three groups are like lower alkyl groups such as methyl or ethyl groups.

Those quaternary ammonium hydroxides having alkyl groups containing from 3 to 12 carbon atoms may have either straight chain alkyl groups or branched chain alkyl groups. Thus there may be used to iso-octyl trimethylammonium hydroxide derived from technical iso-octyl alcohols or from 2,2,4-trimethylpentanol, the dodecyl trimethylammonium hydroxide derived either from lauryl alcohol or branched chain dodecanols or a tetrabutyl ammonium hydroxide in which at least one of the butyl groups is an isobutyl group.

These quaternary ammonium hydroxides are readily prepared from the corresponding salts $R_1 R_2 R_3 R_4 N^+ X^-$, in which $X^-$ is a chloro, bromo, iodo or bisulfate ion, by passage over a basic ion-exchange resin.

In the formylation, the 1-nitropropane and the formaldehyde react in an aqueous medium in the absence of any organic solvent in a molar ratio of 1.1 to 1.0 – 1.1 and in the presence of 0.005 to 0.01 equivalent of the quaternary ammonium hydroxide. The reactants are stirred for a period of time of from 1 to 24 hours at a temperature below 25°C.

This formylation in an aqueous medium gives mainly 2-nitro-n-butanol to the exclusion of concomitant production of 2-nitro-2-ethylpropane-1,3-diol. There is produced a heterogeneous reaction medium in which the lower phase contains 90% of 2-nitro-1-butanol which is free from 2-nitro-2-ethylpropane-1,3-diol.

When the basic organic catalyst which assists the formylation is tertiary amine, the latter is represented by the general formula $N R_1 R_2 R_3$ in which $R_1$, $R_2$ and $R_3$ are like or unlike alkyl groups containing 1 to 4 carbon atoms and are preferably ethyl groups, i.e. the amine is preferably triethylamine.

The 1-nitropropane and the formaldehyde, in a ratio of 1.1 to 1.0 : 1, are reacted in the aqueous medium in the absence of organic solvents but in the presence of substantially 0.01 to 0.03 equivalent of one of the aforesaid tertiary amines, at temperatures between 20° and 45° C. In one procedure the formylation product is concentrated under a reduced pressure of between 50 and 100 torrs at a temperature not exceeding 60° C. The excess of 1-nitropropane is recycled.

The 2-nitro-n-butanol obtained in the presence of a quaternary ammonium hydroxide or a tertiary amine may be hydrogenated in one to two volumes of methanol based upon the nitrobutanol in the presence of a metallic hydrogenation catalyst, such as Raney nickel, palladium and/or platinum.

The hydrogenation may take place using a mixture of hydrogen and nitrogen at a pressure of from 8 to 12 bars. A mixture containing substantially 85% of hydrogen and 15% of nitrogen is especially suitable.

The 2-nitro-1-butanol may be hydrogenated in methanol, preferably in an equal volume thereof, using 10% by weight of Raney nickel as hydrogenation catalyst at a temperature below 70° C.

It is an advantage to neutralise the methanolic medium containing the 2-nitro-n-butanol with 0.5 to 1 equivalent of carbon dioxide gas, which is fed in at the beginning of the hydrogenation, in order to prevent the nitroalcohols from decomposing with regeneration of the starting materials, and to prevent the formaldehyde which is thus liberated from condensing with the amines formed and producing N-methylated aminoalcohols.

After cooling the reaction mixture and filtering off the nickel catalyst, the filtrate is concentrated, and the methanol, water and finally the amino-butanol are distilled. The latter is collected at a temperature between 75° and 85° C at a pressure of 5 to 15 Torr, the temperature of the still not exceeding 130° C.

The purity of the 2-amino-n-butanol is 98% as determined by vapour phase chromatography. The impurities are 2-methyl-2-amino-n-propanol and N-methylated aminoalcohols, the presence of which is revealed by nuclear magnetic resonance spectroscopy. The impurities may be concentrated as a head fraction during a suitable fractionation procedure.

In accordance with a further feature of the invention, the 2-nitro-n-butanol is reductively hydrogenated in substantially 1 to 2 volumes of methanol using a catalyst which is preferably composed of palladium and platinum supported upon carbon. The hydrogenation catalyst is used in a ratio of substantially 0.8 to 5% with respect to the 2-nitrobutanol. In a preferred procedure, the catalyst comprises substantially 5 to 20% by weight of palladium and substantially 5 to 10% by weight of platinum and preferably about 8% of palladium and about 2% of platinum.

The hydrogenation is carried out using a mixture of hydrogen and nitrogen under a pressure of between 8 and 12 bars, at a temperature not exceeding 55° C, preferably between 50° and 55° C. A hydrogenating mixture containing substantially 85% of hydrogen and 15% of nitrogen is particularly suitable.

After cooling and separation by filtration, the catalyst may be re-used a number of times.

The 2-amino-n-butanol obtained is sufficiently pure to be used directly as an intermediate in organic syntheses.

The following examples illustrate the process of the invention.

EXAMPLE 1

This example illustrates the phase transfer catalysis in the presence of a quarternary ammonium hydroxide.

40.9 g (0.46 moles) of 1-nitropropane and 40ml of formaldehyde as a 30% aqueous solution (0.46 mole) are stirred in the presence of 2 ml of a 40% solution of trimethylbenzylammonium hydroxide ("Triton B"). The reaction is exothermic and lasts for 1 hour. At the conclusion of the exothermic reaction, stirring is discontinued and separation of the components of the reaction mixture takes place. The lower phase formed by the 2-nitro-n-butanol is separated and used directly in the hydrogenation. Vapour phase chromatographic analysis and nuclear magnetic resonance spectroscopy indicate that the mixture consists of 10% of 1-nitropropane and 90% of 2-nitro-n-butanol; no 2-nitro-2-ethylpropane-1,3-diol could be detected. The 2-nitro-n-butanol thus obtained is reduced in solution in an equal volume of methanol using 5 g of Raney nickel and a mixture of 85% of hydrogen and 15% of nitrogen under a pressure of 10 bars. The reaction mixture is neutralised with an equivalent of carbon dioxide which is introduced at the beginning of the reduction. The reduction temperature is kept below 70° C. After the reduction is complete, 25.4 g of 2-amino-n-butanol is distilled, representing a yield of 62% based upon the 1-nitropropane used.

EXAMPLE 2 a. Formylation of 1-nitropropane

At a temperature between 30° and 35° C, 345 kg (3870 moles) of 1-nitropropane and 360 liters of an aqueous solution containing 10.6 moles per liter of formaldehyde are stirred together in the presence of 7.6 kg (128.57 moles) of triethylamine. After stirring for 48 hours, the mixture is concentrated by heating at between 50° and 60° C under a pressure of 50 to 100 torrs. There are thus obtained 405 kg of concentrated 2-nitrobutanol and a distillate consisting of 233 kg of water and 61 kg of 1-nitropropane.

b. Hydrogenation of 2-nitro-n-butanol 135 kg of the 2-nitro-n-butanol previously obtained dissolved in 185 kg of methanol is reduced with hydrogen in the presence of 2.5 kg of a catalyst consisting of 8% palladium and 2% platinum supported upon charcoal. The reduction is carried out at a temperature between 50° and 55° C and the pressure of the hydrogenation mixture consisting of 85% of hydrogen and 15% of nitrogen is between 8 and 12 bars. When the absorption of hydrogen has ceased, the catalyst is separated by filtration and re-used for another reduction.

Three successive reductive hydrogenations are carried out under the same reaction conditions. The filtrates from the three runs, which are performed using a total of 405 kg of 2-nitrobutanol, are combined and distilled under reduced pressure. 210 Kg of 2-amino-n-butanol are thus obtained, i.e. 74% relative to the 1-nitropropane used.

The purity of the 2-amino-n-butanol is 95% as determined by vapour phase chromatography; its acid titer is 97%.

We claim:

1. In a process for the production of 2-amino-n-butanol by the formylation of 1-nitropropane and reductive hydrogenation of the resulting 2-nitro-n-butanol, the improvement comprising the steps of:
    contacting 1-nitropropane with formaldehyde, in a molar ratio within the range of 1.1:1.0 to 1.0:1.0, in a stirred aqueous medium which is free from organic solvents and in the presence of a minor proportion of a basic agent which acts both as a catalyst for the formylation reaction and as a surfactant, said basic agent being selected from the group consisting of quaternary ammonium hydroxides and tertiary amines;
    allowing the stirred reaction medium to settle;
    separating the lower phase comprising 2-nitro-n-butanol free from 2-nitro-2-ethylpropane; and
    reductively hydrogenating the separated 2-nitro-n-butanol.

2. The process of claim 1 in which said basic agent is a quaternary ammonium hydroxide present in a molar equivalent of 0.005 to 0.01 relative to the 1-nitropropane employed and the reactants are stirred for a period of time between 1 and 24 hours at a temperature below 25° C.

3. The process of claim 1 in which said basic agent is a trialkylamine, in which each alkyl group contains 1 to 4 carbon atoms, present in a molar ratio of 0.01 to 0.03 relative to the 1-nitropropane employed and the reactants are stirred at a temperature between 20° and 45° C.

4. The process of claim 3 in which the trialkylamine is triethylamine.

5. The process of claim 2 in which said quaternary ammonium hydroxide has the formula $R_1R_2R_3R_4NOH$ in which $R_1$ is an arylsubstituted alkyl group and each of $R_2$, $R_3$ and $R_4$ is a lower alkyl group.

6. The process of claim 2 in which said quaternary ammonium hydroxide is benzyltrimethylammonium hydroxide.

7. In a process for the production of 2-amino-n-butanol by the formylation of 1-nitropropane and reductive hydrogenation of the resulting 2-nitro-n-butanol, the improvement comprising the steps of:
    contacting 1-nitropropane with formaldehyde in a molar ratio within the range of 1.1:1.0 to 1.0:1.0 in a stirred aqueous medium which is free from organic solvents and in the presence of a minor proportion of a basic agent which acts both as a catalyst for the formylation reaction and as a surfactant, said basic agent being selected from the group consisting of quarternary ammonium hydroxides and tertiary amines;

allowing the stirred reaction mixture to settle when the reaction is substantially complete;

separating the lower phase comprising 2-nitro-n-butanol; free from 2-nitro-2-ethylpropane-1,3-dial;

dissolving the separated phase in from once to twice the volume of methanol; and reductively hydrogenating the nitrobutanol under 8 to 12 bars with a gaseous mixture comprising 85% hydrogen and 15% nitrogen in the presence of a metallic hydrogenation catalyst selected from the group consisting of Raney nickel and palladium and platinum supported on a carbon base.

8. The process of claim 7 in which the metallic hydrogenation catalyst is Raney nickel and the hydrogenation is carried out at a temperature below 70° C.

9. The process of claim 7 in which the metallic hydrogenation catalyst is palladium and platinum supported upon a carbon base and the hydrogenation is carried out at a temperature not exceeding 55° C.

10. The process of claim 9, wherein the catalyst is 5–20% palladium and 5–10% platinum.

11. A process in accordance with claim 9, wherein said basic agent is triethylamine present in a molar ratio of 0.01 to 0.03 relative to the 1-nitropropane employed and the reactants are stirred at a temperature between 20° and 45° C and wherein the metallic hydrogenation catalyst comprises about 8% of palladium and about 2% platinum and is utilized at the rate of about 0.8–5% with respect to nitrobutanol.

* * * * *